(12) United States Patent
Boyer et al.

(10) Patent No.: US 7,745,674 B2
(45) Date of Patent: Jun. 29, 2010

(54) ALKYLATION SLURRY REACTOR

(75) Inventors: Christopher C. Boyer, Houston, TX (US); Lawrence A. Smith, Jr., Pasadena, TX (US)

(73) Assignee: Catalytic Distillation Technologies, Pasadena, TX (US)

( * ) Notice: Subject to any disclaimer, the term of this patent is extended or adjusted under 35 U.S.C. 154(b) by 0 days.

(21) Appl. No.: 12/195,016

(22) Filed: Aug. 20, 2008

(65) Prior Publication Data

US 2010/0048966 A1 Feb. 25, 2010

(51) Int. Cl.
*C07C 6/12* (2006.01)
*C07C 2/66* (2006.01)

(52) U.S. Cl. ............... 585/323; 585/467; 585/475; 585/449

(58) Field of Classification Search ............ 585/323, 585/467, 475, 449
See application file for complete search history.

(56) References Cited

U.S. PATENT DOCUMENTS

| | | | |
|---|---|---|---|
| 3,766,290 A * | 10/1973 | Carlson | 585/450 |
| 4,008,290 A | 2/1977 | Ward | |
| 4,083,886 A | 4/1978 | Michalko | |
| 4,371,714 A | 2/1983 | Young | |
| 4,469,908 A | 9/1984 | Burress | |
| 4,891,458 A | 1/1990 | Innes et al. | |
| 5,003,119 A | 3/1991 | Sardina et al. | |
| 5,019,669 A | 5/1991 | Adams et al. | |
| 5,080,871 A | 1/1992 | Adams et al. | |
| 5,118,872 A | 6/1992 | Smith, Jr. et al. | |
| 5,118,897 A | 6/1992 | Khonsari et al. | |
| 5,196,574 A | 3/1993 | Kocal | |
| 5,324,877 A | 6/1994 | West et al. | |
| 5,856,606 A | 1/1999 | Oroskar | |
| 5,902,917 A | 5/1999 | Collins et al. | |
| 5,998,684 A | 12/1999 | Ho et al. | |
| 6,150,578 A | 11/2000 | Ho et al. | |
| 6,315,964 B1 | 11/2001 | Knifton et al. | |
| 6,376,729 B1 | 4/2002 | Merrill et al. | |
| 6,617,481 B1 | 9/2003 | Kulprathipanja et al. | |
| 7,253,331 B2 | 8/2007 | Martens et al. | |

FOREIGN PATENT DOCUMENTS

EP 0485683 A1 5/1992

OTHER PUBLICATIONS

International Search Report with Written Opinion issued in related PCT Application No. PCT/US2009/044420 dated Dec. 30, 2009. (10 pages).

* cited by examiner

*Primary Examiner*—Thuan Dinh Dang
(74) *Attorney, Agent, or Firm*—Osha • Liang LLP

(57) ABSTRACT

A process for alkylation of benzene, including: feeding benzene, a polyalkylate, and a catalyst to a reactor comprising a first and a second reaction zone; reacting the benzene and the polyalkylate in the first reaction zone under transalkylation conditions to form a monoalkylate product; feeding a $C_2$-$C_4$ olefin to the reactor intermediate the first and second reaction zones; reacting benzene and the $C_2$-$C_4$ olefin in the second reaction zone under alkylation conditions to form additional monoalkylate product; recovering an effluent from the reactor, wherein the effluent comprises benzene, the monoalkylate product, any unreacted $C_2$-$C_4$ olefins, heavy hydrocarbons, and the catalyst; separating the catalyst from the effluent; separating the benzene from the monoalkylate product and the heavy hydrocarbons within the liquid effluent; separating the monoalkylate product from the heavy hydrocarbons within the liquid effluent; and recovering the monoalkylate product.

13 Claims, 2 Drawing Sheets

ALKYLATION SLURRY REACTOR

BACKGROUND OF DISCLOSURE

1. Field of the Disclosure

Embodiments disclosed herein relate generally to catalytic alkylation and transalkylation of benzene using a $C_2$-$C_4$ olefin and a heterogeneous catalyst slurry, which can be continuously replaced during operation.

2. Background

Alkylation refers generally to a type of chemical reaction resulting in addition of an alkyl group to an organic compound. Olefins, such as ethylene, propylene, and butylenes, are well-known alkylating agents, frequently used in synthesis of alkylated derivatives. Alkylation of benzene is a commercially important process, used to increase the octane rating of fuel and to produce valuable chemical feedstocks. For example, alkylation of benzene with ethylene may be used to produce ethylbenzene, which may be subsequently converted to styrene. Similarly, alkylation of benzene with propylene may be used to produce cumene, which may be subsequently converted to phenol and acetone.

A typical benzene alkylation reaction is shown below:

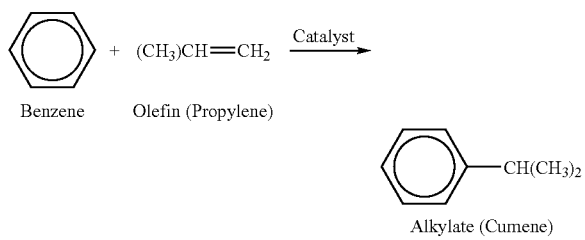

Older alkylation technology, still widely employed in the petrochemical industry, involves the use of a catalyst based on phosphoric acid. Newer technology utilizes non-polluting, non-corrosive, regenerable materials, such as zeolitic molecular sieve catalysts. U.S. Pat. Nos. 4,371,714 and 4,469,908 disclose straight pass alkylation of aromatic compounds using molecular sieve catalysts in fixed beds. However, there are two main problems arising from the use of zeolitic catalysts in alkylation reactions, namely a more rapid deactivation of the zeolitic catalyst due to cooking and poisoning and a higher yield of polyalkylated by-products.

The first problem often results in frequent unit shut downs or other process interruptions, such as for thermal regeneration of the catalyst. U.S. Pat. No. 5,118,897 further discloses a process for reactivating the zeolitic alkylation catalyst by temporary substitution of the olefin supply stream with a hydrogen stream under certain conditions to shorten the thermal catalyst regeneration cycle.

U.S. Pat. No. 5,856,606 discloses a process for alkylating paraffins including a reaction zone containing a pool of liquid maintained at its boiling point and containing a suspended solid catalyst. U.S. Pat. Nos. 5,019,669, 5,080,871 and 5,118,872 disclose a moving bed reaction system for alkylation of aromatic compounds, in which a slurry is produced by adding solid catalyst to the aromatic feed stream into the reactor. The catalyst slurry circulated through the system may be continuously replaced and regenerated during operation, thus reducing the need for unit shut downs. In some embodiments, these patents also suggest inert distillation packing inside the reactive distillation zone and pressure control to adjust the reactor temperature.

The second problem may be addressed by the use of a second reaction zone for transalkylation of polyalkylate by-products with benzene to increase yield of the desired alkylation product. For example, U.S. Pat. No. 4,083,886 describes a process for transalkylation of alkylate aromatic hydrocarbons that uses a zeolitic catalyst in a fixed bed reactor. U.S. Pat. No. 4,891,458 describes the use of beta zeolite for the alkylation or transalkylation of aromatic hydrocarbons with polyalkylate aromatic hydrocarbons. In one embodiment, the process disclosed includes alkylation or transalkylation using a moving bed catalyst with a catalyst regeneration system. In another embodiment, the invention specifies a jacket or condenser type cooler to maintain constant reactor temperature.

Combining alkylation and transalkylation can thus maximize monoalkylate production. Such a combination can be carried out in a process having two reaction zones, one for alkylation and the other for transalkylation, or in a process having a single reaction zone in which alkylation and transalkylation both occur. For example, U.S. Pat. No. 4,008,290 describes a combination process in which the alkylation effluent and the transalkylation effluent are passed from separate reaction zones to a common separation zone, which separates the two effluents into product, by-product, and recycle streams including a recycle benzene stream.

U.S. Pat. No. 5,003,119 describes a combination process for producing monoalkylate aromatics in which the alkylation effluent passes to the transalkylation reaction zone, and the transalkylation effluent passes to a separation zone. In one embodiment, alkylation and transalkylation reactions take place in different reactors. In another embodiment, alkylation and transalkylation reactions takes place either adiabatically or using interstage cooling.

U.S. Pat. No. 5,902,917 describes a process for producing monoalkylate aromatics, wherein a feedstock is instead first fed to a transalkylation zone and the entire effluent from the transalkylation zone is then cascaded directly into an alkylation zone along with an olefin alkylating agent.

U.S. Pat. No. 5,998,684 describes a process for producing alkylate aromatics that operates with an alkylation zone and a transalkylation zone, where the transalkylation zone and the alkylation zone are arranged for series flow and the transalkylation zone effluent is passed with an aromatic containing feed and the olefinic feed, which is preferably propylene or ethylene, to the alkylation zone. In one embodiment, alkylation and transalkylation take place in separate reactors arranged in series.

Although various processes exist for the alkylation and transalkylation of benzene, as described above, there still exists a need in the art for improved processes for the alkylation and transalkylation of benzene and the removal of benzene from various hydrocarbon feeds.

SUMMARY OF THE DISCLOSURE

In one aspect, embodiments disclosed herein relate to a process for alkylation of benzene, including: feeding benzene, a polyalkylate, and a catalyst to a reactor comprising a first and a second reaction zone; reacting the benzene and the polyalkylate in the first reaction zone under transalkylation conditions to form a monoalkylate product; feeding a $C_2$-$C_4$ olefin to the reactor intermediate the first and second reaction zones; reacting benzene and the $C_2$-$C_4$ olefin in the second reaction zone under alkylation conditions to form additional monoalkylate product; recovering an effluent from the reactor, wherein the effluent comprises benzene, the monoalkylate product, any unreacted $C_2$-$C_4$ olefins, heavy hydrocarbons, and the catalyst; separating the catalyst from the effluent; separating the benzene from the monoalkylate product and the heavy hydrocarbons within the liquid effluent; separating the monoalkylate product from the heavy hydrocarbons within the liquid effluent; and recovering the monoalkylate product.

In another aspect, embodiments disclosed herein relate to a system for the alkylation of benzene, including: a reactor comprising a first reaction zone and a second reaction zone; one or more fluid conduits for feeding benzene, polyalkylate, a $C_2$-$C_4$ olefin and a catalyst to the reactor proximate at least one of the first reaction zone and the second reaction zone, wherein the polyalkylate and the benzene are contacted in the presence of the catalyst to form monoalkylate in the first reaction zone, and wherein the benzene and the $C_2$-$C_4$ olefins are contacted in the presence of the catalyst to form additional monoalkylate in the second reaction zone; a fluid conduit for recovering effluent from the reactor, wherein the effluent comprises unreacted benzene, the monoalkylate product, any unreacted $C_2$-$C_4$ olefins, heavy hydrocarbons, and the catalyst; a first separator for separating the catalyst from the liquid effluent; and a separation system for recovering the monoalkylate product from the effluent.

Other aspects and advantages will be apparent from the following description and the appended claims.

DETAILED DESCRIPTION

Figure 1:
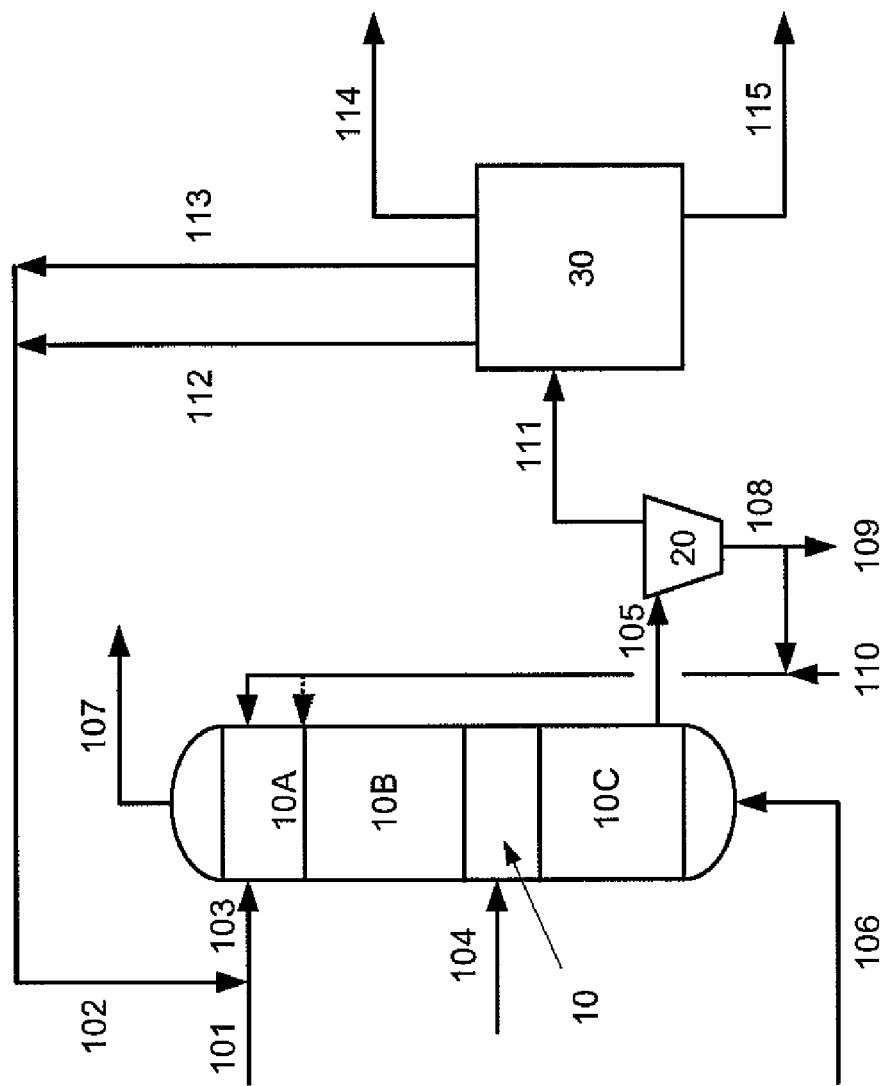
FIG. 1 is a simplified flow diagram of a benzene alkylation and transalkylation process in a slurry reactor according to embodiments disclosed herein.

Embodiments disclosed herein relate to processes for the alkylation and transalkylation of benzene to form ethylbenzene, cumene, butylbenzene, and other alkylate or transalkylate products. More specifically, embodiments disclosed herein relate to a process for the alkylation and transalkylation of benzene in a slurry reactor. In a family of embodiments, the slurry reactor may be a tubular reactor, providing for one or more of heating reactor feeds and temperature control of the transalkylation and alkylation reaction zones.

Olefins

In some embodiments of the alkylation processes described herein, olefins are reacted with aromatic hydrocarbons, more specifically benzene, to form an alkylate product. In one embodiment, olefins for the alkylation of the aromatic hydrocarbon are those containing 2 to 4 carbon atoms, such as ethylene, propylene, butene-1, trans-butene-2 and cis-butene-2, or mixtures thereof.

The olefin feed streams used in various embodiments disclosed herein may also contain certain impurities, such as the corresponding $C_2$ to $C_4$ paraffins. Typically, the impurities, including dienes, acetylenes, water, sulfur compounds or nitrogen compounds which may be present in the olefin feedstock stream, are removed prior to the alkylation and transalkylation reaction to prevent rapid catalyst deactivation. In some cases, however, it may be desirable to add, in a controlled fashion, small amounts of water or nitrogen compounds to optimize catalytic properties.

Alkylation

In embodiments of the alkylation processes disclosed herein, a hydrocarbon feedstock containing aromatics, such as benzene, is reacted with olefins in the presence of an alkylation catalyst to form high-octane gasoline components. In particular, one embodiment described herein involves reaction of benzene with a $C_2$ to $C_4$ olefin to form monoalkylate product in the presence of an alkylation catalyst. The precise process steps and process conditions may vary depending upon the catalyst system used. In another embodiment, a heterogeneous slurry catalyst is used to facilitate the alkylation reaction. For the purpose of illustration and not a limitation of the process, several representative alkylation reactions of olefins with benzene are provided as follows:

1) ethylene+benzene→ethylbenzene
2) propylene+benzene→propylbenzene
3) propylene+benzene→isopropylbenzene (cumene)
4) n-butylene+benzene→butylbenzene
5) isobutylene+benzene→isobutylbenzene In addition to the monoalkylate product, alkylation reactions typically yield other undesirable byproducts in the form of heavy hydrocarbons, including but not limited to, polyalkylate, heavy flux oil (including components that will not transalkylate), and polymerized feed olefins.

Transalkylation

Transalkylation reactions may be used to produce monoalkylate product by reacting benzene with polyalkylate. When transalkylation is desired, the transalkylating agent is a polyalkylate aromatic hydrocarbon containing two or more alkyl groups that each may have from 2 to about 4 carbon atoms. For example, suitable polyalkylate aromatic hydrocarbons include di-, tri- and tetra-alkyl aromatic hydrocarbons, such as diethylbenzene, triethylbenzene, diethylmethylbenzene (diethyltoluene), diisopropylbenzene, triisopropylbenzene, diisopropyltoluene, dibutylbenzene, and the like. In one particular embodiment, the polyalkylate aromatic hydrocarbon is diisopropylbenzene, which reacts with benzene to form cumene (isopropylbenzene).

Reaction products which may be obtained from the transalkylation process of benzene include, but are not limited to, ethylbenzene from the reaction of benzene with either ethylene or polyethylbenzenes; cumene from the reaction of benzene with propylene or polyisopropylbenzenes; ethyltoluene from the reaction of toluene with ethylene or polyethyltoluenes; cumenes from the reaction of toluene with propylene or polyisopropyltoluenes; and sec-butylbenzene from the reaction of benzene and n-butylene or polybutylbenzenes. For the purpose of illustration and not a limitation of the process, several representative transalkylation reactions of polyalkylate with benzene are provided as follows:

1) diethylbenzene+benzene→2 ethylbenzene
2) di-isopropylbenzene+benzene→2 isopropylbenzene (cumene)
3) dibutylbenzene+benzene→2 butylbenzene Types of Reactors Various types of reactors can be used in the process of alkylation as well as transalkylation. Selection of the type of reactor for use in alkylation or transalkylation reaction may depend on a number of factors, including the desired mode of operation, throughput volume, and reaction control parameters, such as residence time and product yield.

Large scale industrial processes typically use continuous flow reactors, either as fixed bed or as moving bed reactors. Moving bed reactors typically operate either with concurrent or countercurrent catalyst, olefin, and hydrocarbon flows. These reactors may contain a single catalyst bed or multiple beds and may be equipped for the interstage addition of olefins and interstage cooling. Interstage olefin addition and more nearly isothermal operation enhance product quality and catalyst life. A moving bed reactor makes possible the continuous removal of spent catalyst for regeneration and replacement by fresh or regenerated catalysts.

In a moving bed reactor, alkylation is completed in a relatively short reaction zone following the introduction of olefin. Ten to thirty percent of the reacting aromatic molecules may be alkylated more than once. Transalkylation is a slower reaction which occurs both in the transalkylation and the alkylation reaction zones. If transalkylation proceeds to equilibrium, better than 90 wt % selectivity to monoalkylated product is generally achieved. Thus, transalkylation increases the yield of monoalkylated product by reacting the polyalkylated products with benzene.

In one embodiment, both the alkylation and the transalkylation reaction processes are carried out in a single tubular heat exchanged reactor, where the reaction slurry, containing the liquid feed and the suspended heterogeneous alkylation catalyst, flows through one side of the tubular reactor and a heat transfer medium flows through the other side of the tubular reactor to capture at least a portion of the heat of reaction. In particular, the alkylation and the transalkylation reaction zones are located in series within the tubular reactor, where the alkylation reactor zone is located downstream of the transalkylation reaction zone, and where the olefin feed is added intermediate to the transalkylation and the alkylation reaction zones.

The benefits of both alkylation and transalkylation reactions taking place in the same reactor include capital cost savings, reducing the amount of necessary process equipment, auxiliary structures and transfer piping requirements; operating cost savings, using a lesser volume of catalyst slurry to fill the smaller system; and the smaller overall unit size, especially where construction space is limited.

Feed Location

The exact locations of the olefin and aromatic hydrocarbon feed streams will depend on the particular feed compositions, the desired product, and the type of system. For instance, the location of feed streams with respect to reaction zones may be strategically selected to increase product quality and yield.

In one embodiment, such as where transalkylation and alkylation are performed in distinct reactors, the olefin feed, in a vapor phase, is added below the alkylation reaction zone and flows countercurrent to the catalyst-containing hydrocarbon slurry. In another embodiment, the olefin feed to the reaction is made into the upper end of the reactor to separate the unreacted organic aromatic compound form the alkylation product, thereby ensuring good mixing and complete olefin conversion.

In yet another embodiment, alkylation and transalkylation reaction zones are located in series within the same reactor, where the olefin feed is added between the two zones— downstream of the transalkylation zone, but upstream of the alkylation zone. Multiple olefin feed points may also be used, such as to distribute the concentration of olefin along the alkylation reaction zone.

Catalyst

Zeolitic catalysts may be used in embodiments disclosed herein for the alkylation and transalkylation of aromatic hydrocarbons, in particular for benzene alkylation and transalkylation, and various catalysts may exhibit superior activity and selectivity.

Zeolites useful in embodiments disclosed herein may include natural and synthetic zeolites. Acidic crystalline zeolitic structures useful in embodiments disclosed herein may be obtained by the building of a three dimensional network of $AlO_4$ and $SiO_4$ tetrahedra linked by the sharing of oxygen atoms. The framework thus obtained contains pores, channels and cages or interconnected voids. As trivalent aluminum ions replace tetravalent silicon ions at lattice positions, the network bears a net negative charge, which must be compensated for by counterions (cations). These cations are mobile and may occupy various exchange sites depending on their radius, charge or degree of hydration, for example. They can also be replaced, to various degrees, by exchange with other cations. Because of the need to maintain electrical neutrality, there is a direct 1:1 relationship between the aluminum content of the framework and the number of positive charges provided by the exchange cations. When the exchange cations are protons, the zeolite is acidic. The acidity of the zeolite is therefore determined by the amount of proton exchanged for other cations with respect to the amount of aluminum.

Alkylation catalysts that may be used in some embodiments disclosed herein may include zeolites having a structure type selected from the group consisting of BEA, MOR, MTW, and NES. Such zeolites include mordenite, ZSM4, ZSM-12, ZSM-20, offretite, gmelinite, beta, NU-87, and gottardite. Clay or amorphous catalysts including silica-alumina and fluorided silica-alumina may also be used. Further discussion of alkylation catalysts may be found in U.S. Pat. Nos. 5,196,574; 6,315,964 and 6,617,481. Various types of zeolitic catalysts may be used for alkylation as well as other types of catalytic refinery processes. FCC processes may utilize at least one of a type Y, Beta, and ZSM-5, for example. The FCC zeolitic catalyst typically contains three parts: the zeolite, typically about 30 to 50 wt. % of the catalyst particle, an active matrix, and a binder. In one embodiment, the particle size of the FCC catalyst may be between 50 and 60 microns. In another embodiment, the zeolitic catalyst may initially come in ammonium form, which may be converted to the $H^+$ form by heating at over 300° C. before being used as an alkylation catalyst. One must take care not to overheat the catalyst prior to alkylation, because excessive temperature may dealuminate the zeolite and shrink the ring structures, which may reduce the activity for alkylation. In addition to zeolitic catalyst, inorganic catalyst, such as sulfated zirconia or tungstated zirconia, may be used for alkylation as well.

In some embodiments, suitable catalysts for alkylation and transalkylation may include metal stabilized catalysts. For example, such catalysts may include a zeolite component, a metal component, and an inorganic oxide component. The zeolite may be a pentasil zeolite, which include the structures of MFI, MEL, MTW, MTT and FER (IUPAC Commission on Zeolite Nomenclature), MWW, a beta zeolite, or a mordenite. The metal component typically is a noble metal or base metal, and the balance of the catalyst may be composed of an inorganic oxide binder, such as alumina. Other catalysts having a zeolitic structure that may be used in embodiments disclosed herein are described in U.S. Pat. No. 7,253,331, for example.

Certain zeolitic catalyst that may be used in an FCC reactor may also be used in an alkylation reactor according to embodiments disclosed herein. In one embodiment, a fresh MWW type zeolitic catalyst may be used to facilitate aromatics alkylation, and when spent, it may be further fed to an FCC unit as an equilibrium catalyst. In another embodiment, an FCC catalyst may be fed to an alkylation reactor as make-up catalyst.

In one particular embodiment disclosed herein, the zeolite crystal is mixed with a binder and extruded into a pellet that is suitable for use in both alkylation and transalkylation reactions. In another embodiment, the zeolite catalyst crystal or pellets may be suspended in a liquid phase, wherein the catalyst particle size is small enough to be suspended in the liquid phase, yet large enough for removal by conventional separation techniques, such as settling, cycloning and filtration.

Catalyst powder may be suspended directly in the liquid feed stream to the alkylation reactor, such as the benzene feed, or may be carried to the reactor separately, such as suspended in an inert hydrocarbon. The concentration of catalyst in the slurry can vary over a wide range, depending on such process variables as the catalyst particle size, particle density, surface area, olefin feed rate, ratio of aromatic to olefin, temperature and catalyst activity. The competing considerations of reactivity and physical dynamics of the reactants in a particular system may necessitate adjustment of several variables to approach a desired result.

Certain zeolitic catalysts may be used to facilitate both alkylation and transalkylation reactions. In one embodiment, both alkylation and transalkylation reactions are conducted using the same zeolitic catalyst in the same reaction zone; in another embodiment, the same zeolitic catalyst is used for both reactions, however, the alkylation and the transalkylation reactions take place in two separate reaction zones, located in series within the same reactor; in another embodiment. One particular catalyst found to effectively facilitate both alkylation and transalkylation is zeolite beta ($\beta$).

In one embodiment, a catalyst slurry may be formed by adding solid zeolite catalyst particles into a liquid stream. For example, the catalyst slurry along with fresh aromatic feed may be added to the reactor, upstream of the transalkylation reaction zone. The catalyst slurry may be withdrawn from the bottom of the reactor, downstream of the alkylation reaction zone and may be concentrated by separating a portion of the liquid phase containing the alkylate product. The concentrated catalyst slurry may also be recycled to the reactor. Additionally, fresh or regenerated catalyst may be added to and spent catalyst purge may be withdrawn from the catalyst recycle stream while in operation. Conventional methods for separating the solid catalyst include, but are not limited to, filtration, settlement, and centrifugation. Spent catalyst withdrawn from the catalyst recycle stream may be further regenerated and returned into the system without interrupting the reactor operation.

One benefit of using a heterogeneous catalyst slurry reactor over a fixed catalyst bed reactor is reduction in catalyst fouling rate due to cooking related to flow maldistribution, which may lead to rapid catalyst deactivation. Another benefit of using a heterogeneous catalyst slurry reactor instead of a fixed catalyst bed reactor is that the spent catalyst may be regenerated and replaced while the unit is on-line, without causing time-consuming and maintenance-intensive shut-downs or interrupting production.

Another benefit of using the same heterogeneous catalyst slurry for both alkylation and transalkylation in the same reactor includes the cost savings and simplified operation associated with handling a single catalyst-containing fluid and a single regeneration system for both reaction zones.

To the best of the inventors' knowledge, use of a single catalyst slurry feed for sequential alkylation and transalkylation in the same reactor, as disclosed herein, has previously not been performed. Typical processes including both alkylation and transalkylation, as described above, generally include separation and recovery of catalyst and alkylate products prior to transalkylation of polyalkylate by-products using a separate and distinct catalyst bed and/or catalyst feed. The inventors have surprisingly found that catalysts useful for both alkylation and transalkylation, as described herein, may have sufficient activity to perform these reactions sequentially, without the need for intermediate catalyst separation or regeneration. Thus, processes and systems for the transalkylation and alkylation of benzene as disclosed herein may be performed in a single tubular reactor, allowing for process efficiencies and economies, such as heat recovery and integration, decreased capital and operating expenditures, and other benefits as will be apparent to one skilled in the art.

Reaction Conditions

The alkylation and transalkylation reaction conditions are generally selected to yield the desired alkylation products without undue detrimental effects upon the catalyst or alkylation reactants, such as catalyst deactivation, excessive side reactions, cracking, polymerization, or carbon formation. Generally, the reaction temperature may range from 40° C. to 320° C. (100° F. to 600° F.). In one particular embodiment, favorable operating temperature may be in the 90° C. to 200° C. (200° F. to 400° F.) range. The temperature may vary depending on the reactants and product. In the case of cumene production, the typical reaction temperature range is 120° C. to 190° C. (250° F. to 375° F.), which helps reduce the product impurities.

The reaction pressure should be sufficient to maintain at least a partial liquid phase in order to retard catalyst fouling. This is typically 400 kPa to 7000 kPa (about 50 psig to about 1000 psig), depending on the feedstock and reaction temperature. In one particular embodiment, favorable operating pressure may be found in the 1500 kPa to 3000 kPa (about 200 psig to about 400 psig) range.

In moving bed reactors, where the catalyst is mixed with the liquid feed stream to produce a slurry, the reactor pressure is generally maintained high enough to ensure minimal evaporation losses at the desired reactor operating temperature. In such systems, it is imperative that the catalyst stays wetted at all times to prevent rapid catalyst fouling and premature deactivation. Premature catalyst deactivation may significantly increase unit operating costs by one or more of: requiring more frequent replacement of spent catalyst with either fresh or regenerated catalyst; increase unit downtime in case of reactors using fixed catalyst beds, which cannot be replaced on-line; and cause production of undesirable impurities and other contaminants that may decrease the value of the reaction product stream. In case of catalyst regeneration, significant capital cost may be required to increase the catalyst regeneration unit capacity in order to handle the additional catalyst regeneration load due to rapid catalyst deactivation in the alkylation reactor.

Some particular types of impurities include oligomers and polymers that may result from undesirable polymerization reactions of olefins contained in the feed. Polymerization of olefins contained in the feed decreases the effective yield of the desired alkylate product, produces additional impurities that must be further separated, and raises the operating costs by increasing the amount of olefins required.

In one embodiment of the present alkylation process, both alkylation and transalkylation reactions take place at a temperature in the range from about 130-170° C., such as about 150° C. (about 300° F.), and a pressure in the range from about 1900–2500 kPa, such as about 2200 kPa (about 300 psig), in two separate reaction zones within a single reactor unit. At these operating conditions, favorable product quality and yield may be achieved from a certain feedstock composition, while at the same time, acceptable catalyst activity was maintained.

Heat Transfer and Reactor Temperature Control

In conducting exothermic reactions, such as alkylation and transalkylation, heat exchange systems, such as reactor cooling devices, may be used to remove the heat of reaction in order to maintain stable reaction conditions favorable to product quality and yield. Heat exchange systems may also be used to prevent potentially dangerous conditions, such as a temperature or pressure excursion or a runaway reaction outside the safe operating limits of the mechanical process equipment.

In one embodiment, transalkylation reaction processes may be carried out in a tubular heat exchange reactor, wherein a cold heat transfer medium enters the tubular reactor, continuously flows through one side of the tubular reactor to remove at least a portion of the heat of reaction and to maintain a stable reactor temperature, and exits as hot heat transfer medium downstream of the tubular reactor. In another embodiment, a flow control device is used to control flow of the heat transfer medium through the tubular reactor in order to maintain the desired reactor temperature.

Another benefit of the heat transfer system being an integral part of the tubular reactor as opposed to an external heat transfer device includes capital cost savings from using less mechanical process equipment and piping and operating cost savings resulting from lower pumping costs and lower heat losses from equipment and piping.

Further energy cost savings from using a tubular reactor may be achieved by capturing the heat of alkylation reaction in a heat transfer medium that may be used in various heat integration applications. For example, recovered heat may be used in downstream separations.

One such heat integration benefit involves using the heat of alkylation reaction recovered in a heat transfer medium to pre-heat the alkylation reactor feed. For example, the hot heat transfer medium effluent from the tubular reactor may be sent to a feed preheat zone, wherein the reactor feed, comprising fresh benzene, benzene recycle, and polyalkylate recycle, may be heated to the desired temperature prior to entering the transalkylation reaction zone. In one embodiment, the feed preheat zone is contained within the tubular reactor, upstream of the transalkylation reaction zone. In another embodiment, the feed preheat zone is contained in an external heat transfer system.

One benefit of a feed preheat system is to allow better control and uniformity of the temperature inside the reactor. Another benefit of the feed preheat system to pre-heat the reactor feed is potentially improved product yield, as the feed enters the reactor closer to the reaction temperature and thus has more time to react. Another significant benefit of housing the feed preheat system in the same vessel as the transalkylation and the alkylation reaction zones includes capital cost savings from using less mechanical equipment and piping and operating cost savings resulting from lower pumping costs and heat losses.

Process Description

Referring now to FIG. 1, a process for benzene alkylation and transalkylation according to embodiments disclosed herein is illustrated. Fresh benzene in flow line 101 may be combined with any recycled benzene and polyalkylate in flow line 102 and may be fed via flow line 103 to the feed preheat zone 10A within the tubular reactor 10, where it may be heated with hot heat transfer medium. Alternatively, the feed preheat zone may be contained in an external heat transfer system (not shown). Components in flow line 103 may further flow from the preheat zone 10A to transalkylation reaction zone 10B of tubular reactor 10. Catalyst slurry may be fed to the feed preheat zone 10A or to the transalkylation reaction zone 10B of the tubular reactor via flow line 108. The polyalkylate and benzene may react in transalkylation reaction zone 10B to form monoalkylate product. A $C_2$ to $C_4$ olefin or a mixture thereof may be fed to tubular reactor 10 via line 104 downstream of transalkylation reaction zone 10B but upstream of alkylation reaction zone 10C. The $C_2$ to $C_4$ olefin(s) may react to near completion with benzene in alkylation reaction zone 10C to form monoalkylate product. Cold heat transfer medium may be fed via flow line 106 to the cooling side of tubular reactor 10 to capture at least a portion of the heat of reaction in alkylation reaction zone 10C and transalkylation reaction zone 10B. Hot transfer medium effluent from the tubular reactor 10 containing the heat of reaction may be recovered downstream of the feed preheat zone 10A via flow line 107. The reactor effluent may be recovered via flow line 105 downstream of the alkylation reaction zone 10C of tubular reactor 10.

The reactor effluent in flow line 105 may be sent to a catalyst separating system 20 for separating catalyst from liquid effluent. The concentrated catalyst slurry separated from the reactor effluent in catalyst separating system 20 may be recovered in flow line 108 and at least a portion may be recycled to preheat zone 10A or transalkylation reaction zone 10B at the top of tubular reactor 10. Catalyst may be purged from catalyst recycle flow line 108 via flow line 109 for regeneration. Fresh catalyst, if necessary, may be added to catalyst recycle flow line 108 via flow line 10. Liquid effluent separated from reactor effluent in catalyst separating system 20 may be recovered via flow line 111.

The liquid effluent from catalyst separating system 20, including the alkylated aromatics, may be fed via flow line 111 to separation system 30, where the liquid effluent may be separated into monoalkylate product, benzene, polyalkylate, and flux oil, which may be recovered via flow lines 114, 112, 113 and 115, respectively.

The benzene recovered via flow line 112 and the polyalkylate recovered via flow line 113 may be combined via flow line 102 and recycled back to tubular reactor 10 to achieve higher product yield. The recycle flow line 102 may be combined with fresh benzene flow line 101 and sent to feed preheat zone 10A within the tubular reactor 10, where hot heat transfer medium may be used to pre-heat the benzene and the polyalkylate recycle. Alternatively, the feed preheat zone may be contained in an external heat transfer system.

Figure 2:
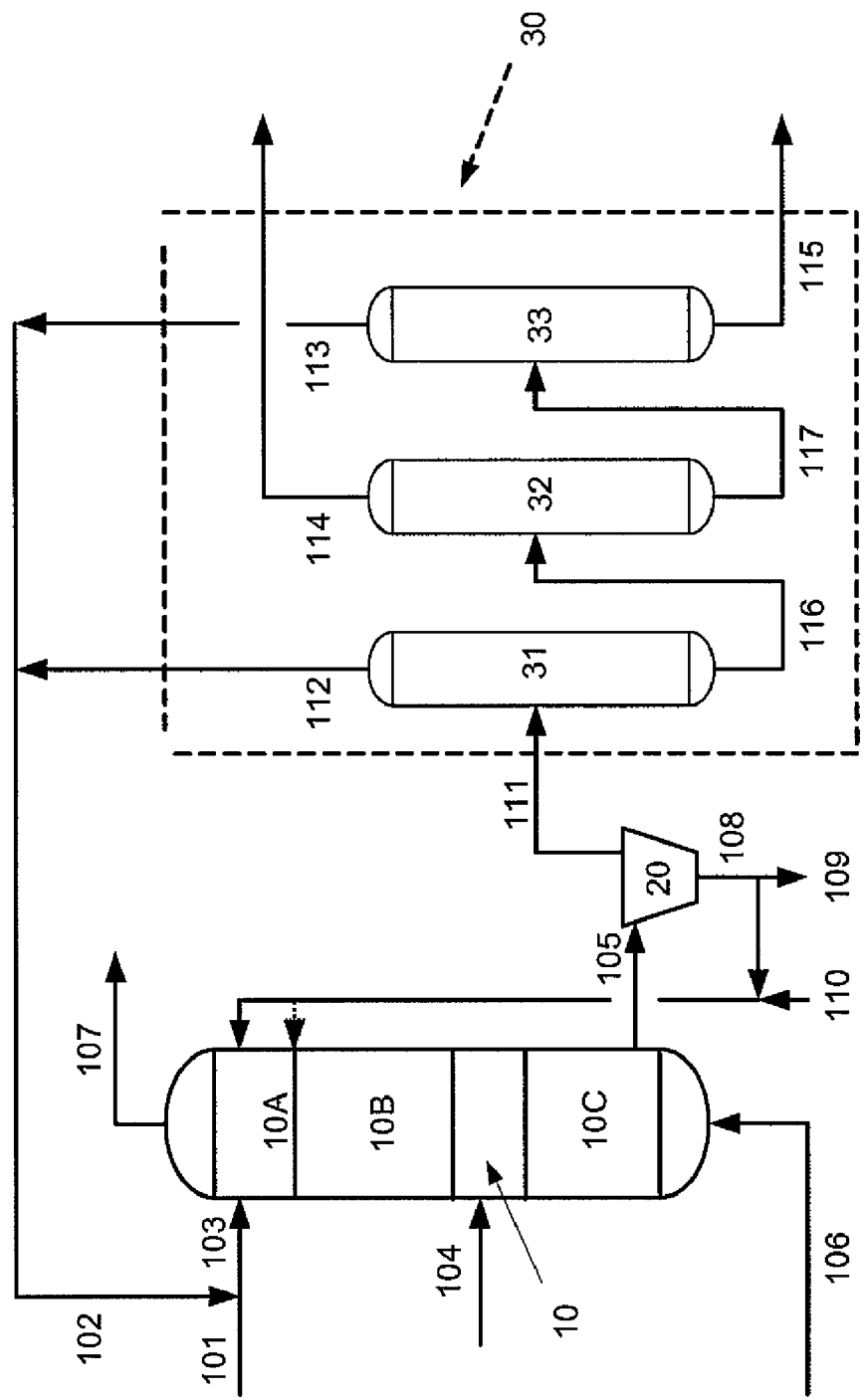
FIG. 2 is a simplified flow diagram of a benzene alkylation and transalkylation process in a slurry reactor according to embodiments disclosed herein.

Referring now to FIG. 2, another process for benzene alkylation and transalkylation according to embodiments disclosed herein is illustrated, where like numerals represent like parts. In this embodiment, a separation system 30 is illustrated as including multiple distillation columns for the recovery and/or recycle of reactants, products, and by-products.

In one embodiment of separation system 30, individual component separations may take place in separators 31, 32 and 33. Liquid effluent from catalyst separating system 20 may be sent via flow line 111 to separator 31, wherein benzene may be separated from monoalkylate product and heavy hydrocarbons contained in the liquid effluent. Benzene may be recovered from the top of separator 31 as an overheads fraction via flow line 112. Monoalkylate product and heavy hydrocarbons, containing polyalkylate and flux oil, may be recovered from the bottom of separator 31 via flow line 116.

Monoalkylate product and heavy hydrocarbons in flow line 116 may be further fed to separator 32, wherein monoalkylate product is separated from heavy hydrocarbons. Monoalkylate product may be recovered from the top of separator 32 via flow line 114, while heavy hydrocarbons, containing polyalkylate and flux oil, may be recovered from the bottom of separator 32 via flow line 117.

Heavy hydrocarbons may be fed via flow line 117 to separator 33, wherein polyalkylate is separated from flux oil. Polyalkylate may be recovered from the top of separator 33 via flow line 113, while flux oil may be recovered from the bottom of separator 33 via flow line 115.

The benzene recovered via flow line 112 and the polyalkylate recovered via flow line 113 may be combined via flow line 102 and recycled back to tubular reactor 10 to achieve higher product yield. The recycle flow line 102 may be combined with fresh benzene flow line 101 and sent to feed preheat zone 10A within the tubular reactor 10, where hot heat transfer medium may be used to pre-heat the benzene and the polyalkylate recycle. Alternatively, the feed preheat zone may be contained in an external heat transfer system.

As described above, embodiments disclosed herein include a process for the sequential transalkylation and alkylation of benzene in a single reactor. Advantageously, embodiments disclosed may provide for efficient reaction of benzene to produce high-octane monoalkylate products. The sequential reaction using a slurry catalyst may allow a decrease in piece count, reducing the capital expenditures and operating expenses typically encountered for a combined alkylation/transalkylation process. Additionally, use of a tubular reactor in various embodiments may provide for heat integration and reactor temperature control, thus decreasing utility requirements and improving selectivity of the process for monoalkylate products.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed:

1. A process for alkylation of benzene, comprising:
   feeding benzene, a polyalkylate, and a catalyst to a reactor comprising a first and a second reaction zone;
   reacting the benzene and the polyalkylate in the first reaction zone under transalkylation conditions to form a monoalkylate product;
   feeding a $C_2$-$C_4$ olefin to the reactor intermediate the first and second reaction zones;
   reacting benzene and the $C_2$-$C_4$ olefin in the second reaction zone under alkylation conditions to form additional monoalkylate product;
   recovering an effluent from the reactor, wherein the effluent comprises benzene, the monoalkylate product, any unreacted $C_2$-$C_4$ olefins, heavy hydrocarbons, and the catalyst;
   separating the catalyst from the effluent;
   separating the benzene from the monoalkylate product and the heavy hydrocarbons within the liquid effluent;
   separating the monoalkylate product from the heavy hydrocarbons within the liquid effluent;
   recovering the monoalkylate product.

2. The process according to claim 1, further comprising recovering at least a portion of heat of reaction in a heat transfer medium to control a temperature of at least one of the first reaction zone and the second reaction zone.

3. The process according to claim 2, wherein the reactor further comprises a pre-heat section, the process further comprising pre-heating at least one of benzene and the polyalkylate in the pre-heat section prior to the first reaction zone.

4. The process according to claim 1, further comprising recycling at least a portion of the recovered catalyst to the first reaction zone.

5. The process according to claim 1, wherein the catalyst comprises solid zeolite particles.

6. The process according to claim 4, further comprising at least one of adding fresh catalyst to the first reaction zone and purging spent catalyst from the recycle.

7. The process according to claim 1, wherein the heavy hydrocarbons in the effluent comprise polyalkylate and flux oil.

8. The process according to claim 7, further comprising separating the polyalkylate from the heavy hydrocarbons.

9. The process according to claim 8, further comprising recycling the polyalkylate to the reactor as the polyalkylate feed.

10. The process according to claim 1, further comprising recycling at least a portion of the benzene separated from the monoalkylate to the reactor.

11. The process according to claim 1, wherein the $C_2$-$C_4$ olefin is propylene.

12. The process according to claim 1, wherein the monoalkylate product comprises at least one of cumene, ethylbenzene, and butyl benzene.

13. The process according to claim 1, further comprising feeding additional $C_2$-$C_4$ olefin to the reactor within the second reaction zone.

* * * * *